United States Patent [19]

Berg et al.

[11] Patent Number: 5,190,619
[45] Date of Patent: Mar. 2, 1993

[54] SEPARATION OF 3-METHYL-2-BUTANONE FROM FORMIC ACID BY EXTRACTIVE DISTILLATION WITH DMSO

[75] Inventors: Lloyd Berg, 1314 S. 3rd Ave., Bozeman, Mont. 59715; George Bentu, Bozeman, Mont.

[73] Assignee: Lloyd Berg, Bozeman, Mont.

[21] Appl. No.: 860,418

[22] Filed: Mar. 30, 1992

[51] Int. Cl.⁵ .................... B01D 3/40; C07C 45/83; C07C 53/02
[52] U.S. Cl. ........................ 203/51; 203/56; 203/57; 203/60; 203/61; 203/62; 203/63; 562/609; 568/410
[58] Field of Search ............... 203/51, 57, 61, 62, 203/60, 63, 56; 568/410; 562/609

[56] References Cited

U.S. PATENT DOCUMENTS

| | | | |
|---|---|---|---|
| 3,013,954 | 12/1961 | Pacoud et al. | 203/62 |
| 4,459,178 | 7/1984 | Berg et al. | 203/51 |
| 4,793,901 | 12/1988 | Berg et al. | 568/410 |
| 4,840,707 | 6/1989 | Berg et al. | 568/410 |
| 4,861,436 | 8/1989 | Berg et al. | 568/410 |

Primary Examiner—Wilbur Bascomb, Jr.

[57] ABSTRACT

3-Methyl-2-butanone cannot be separated from formic acid by distillation because of the presence of the maximum boiling azeotrope. 3-Methyl-2-butanone can be readily removed from formic acid by extractive distillation using dimethylsulfoxide (DMSO). Typical effective agents are: DMSO and heptanoic acid; DMSO, octanoic acid and butyl benzoate.

1 Claim, No Drawings

SEPARATION OF 3-METHYL-2-BUTANONE FROM FORMIC ACID BY EXTRACTIVE DISTILLATION WITH DMSO This application is related to Application Ser. No. 07/389,221, abandoned.

FIELD OF THE INVENTION

This invention relates to a method for separating 3-methyl-2-butanone from formic acid using dimethylsulfoxide as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reached the stillpot. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

3-Methyl-2-butanone, B.P.=95.4° C. and formic acid, B.P.=101° C. form a maximum azeotrope boiling at 102° C. and containing 85% formic acid. Extractive distillation would be an attractive method of separation of 3-methyl-2-butanone from formic acid if agents can be found that (1) will enhance the relative volatility of 3-methyl-2-butanone to formic acid and (2) are easy to recover from the formic acid, that is, form no azeotrope with formic acid and boil sufficiently above formic acid to make separation by rectification possible with only a few theoretical plates. Mixtures forming azeotropes are impossible to separate completely by distillation because the azeotrope is always formed.

Extractive distillation typically requires the adition of an equal amount to twice as much extractive agent as the 3-methyl-2-butanone—formic acid on each plate of the rectification column. The extractive agent should be heated to about the same temperature as the plate on to which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

Berg, U.S. Pat. No. 4,692,219 separated formic acid from acetic acid by extractive distillation. Extractive distillation was used by Berg, U.S. Pat. No. 4,735,690 to remove water and impurities from formic acid and Berg, U.S. Pat. No. 4,793,901 to break the 2-pentanone—formic acid azeotrope.

OBJECTIVE OF THE INVENTION

The object of this invention is to provide a process or method of extractive distillation that will enhance the relative volatility of 3-methyl-2-butanone from formic acid in their separation in a rectification column. It is a further object of this invention to identify suitable extractive distillation agents that will separate the 3-methyl-2-butanone—formic acid mixture and make possible the production of pure 3-methyl-2-butanone and formic acid by rectification. It is a further object of this invention to identify certain amides which in addition to the above constraints, are stable, can be separated from formic acid by rectification with relatively few theoretical plates and can be recycled to the extractive distillation column and reused with little or no decomposition.

SUMMARY OF THE INVENTION

The objects of the invention are provided by a process for separating 3-methyl-2-butanone from formic acid which entails the use of dimethylsulfoxide admixed with certain oxygenated organic compounds as the agents in extractive distillation.

TABLE 1

| Effective Extractive distillation Agents Containing DMSO | | | | |
|---|---|---|---|---|
| Compounds | Ratios | | Relative Volatilities | |
| Dimethylsulfoxide (DMSO), Benzoic acid | $(1/2)^2$ | $(3/5)^2$ | 5.2 | 4.3 |
| DMSO, Decanoic acid | " | " | 4.3 | 4.1 |
| DMSO, Glutaric acid | " | " | 4.2 | 1.5 |
| DMSO, Heptanoic acid | " | " | 4.2 | 4.5 |
| DMSO, Hexahydro phthalic acid | " | " | 4.1 | 2.0 |
| DMSO, Hexanoic acid | " | " | 4.3 | 3.0 |
| DMSO, Itaconic acid | " | " | 3.2 | 3.6 |
| DMSO, Myristic acid | " | " | 2.0 | 1.6 |
| DMSO, Octanoic acid | " | " | 3.5 | 4.2 |
| DMSO, Neodecanoic acid | " | " | 2.4 | 3.9 |

TABLE 1-continued
Effective Extractive distillation Agents Containing DMSO

| Compounds | Ratios | | Relative Volatilities | |
|---|---|---|---|---|
| DMSO, p-Nitrophenyl acetic acid | " | " | 4.5 | 3.0 |
| DMSO, Pelargonic acid | " | " | 4.5 | 4.7 |
| DMSO, Phenyl acetic acid | " | " | 5.1 | 6.1 |
| DMSO, o-Toluic acid | " | " | 3.3 | 6.0 |
| DMSO, m-Toluic acid | " | " | 4.7 | 3.9 |
| DMSO, Benzoic acid, Isophorone | $(1/3)^3$ | $(2/5)^3$ | 3.5 | 5.3 |
| DMSO, Decanoic acid, Cyclohexanone | " | " | 2.1 | 1.7 |
| DMSO, Glutaric acid, Methyl salicylate | " | " | 1.7 | 1.7 |
| DMSO, Heptanoic acid, Ethyl benzoate | " | " | 2.4 | 3.0 |
| DMSO, Hexanoic acid, Methyl benzoate | " | " | 2.6 | 3.1 |
| DMSO, Itaconic acid, Methyl salicylate | " | " | 3.1 | 2.1 |
| DMSO, Myristic acid, 2-Methoxyethyl ether | " | " | 1.8 | 1.6 |
| DMSO, Neodecanoic acid, Acetophenone | " | " | 3.2 | 2.0 |
| DMSO, p-Nitropenyl acetic acid, Hexyl acetate | " | " | 3.6 | 2.2 |
| DMSO, Octanoic acid, Butyl benzoate | " | " | 4.0 | 4.6 |
| DMSO, Pelargonic acid, Adiponitrile | " | " | 3.8 | 2.2 |
| DMSO, Phenyl acetic acid, Diisobutyl ketone | " | " | 1.8 | 3.5 |
| DMSO, o-Toluic acid, Ethyl phenyl acetate | " | " | 2.9 | 3.3 |
| DMSO, m-Toluic acid, Diethyl maleate | " | " | 1.3 | 2.9 |

TABLE 2
Data From Run Made In Rectification Column

| Agent | Column | Time, hrs. | Weight % Ketone | Weight % Formic acid | Relative Volatility |
|---|---|---|---|---|---|
| 50% DMSO, 50% Heptanoic acid | Overhead Bottoms | ½ | 57.4 23.3 | 42.6 76.7 | 1.33 |
| 50% Heptanoic acid | Overhead Bottoms | 1¼ | 55 15.4 | 45 84.6 | 1.44 |

DETAILED DESCRIPTION OF THE INVENTION

We have discovered that dimethylsulfoxide (DMSO) when admixed with other high boiling organic compounds, will effectively negate the azeotrope of 3-methyl-2-butanone and formic acid and permit the separation of pure 3-methyl-2-butanone from formic acid by rectification when employed as the agent in extractive distillation. Table 1 lists the mixtures containing DMSO in the proportions that we have found to be effective. The data in Table 1 was obtained in a vapor-liquid equilibrium still. In each case, the starting material was 25% 3-methyl-2-butanone, 75% formic acid. The ratios are the parts by weight of extractive agent used per part of 3-methyl-2-butanone—formic acid mixture. The relative volatilities are listed for each of the two ratios employed. The compounds which are effective when used in mixtures with DMSO are benzoic acid, decanoic acid, glutaric acid, heptanoic acid, hexahydro phthalic acid, hexanoic acid, itaconic acid, myristic acid, octanoic acid, neodecanoic acid, p-nitrophenyl acetic acid, pelargonic acid, phenyl acetic acid, o-toluic acid, m-toluic acid, isophorone, cyclohexanone, methyl salicylate, ethyl benzoate, methyl benzoate, 2-methoxyethyl ether, acetophenone, hexyl acetate, butyl benzoate, adiponitrile, diisobutyl ketone, ethyl phenyl acetate and diethyl maleate.

The two relative volatilities shown in Table 1 correspond to the two different ratios investigated. For example, in Table 1, one half part of DMSO with one half part of benzoic acid with one part of the 3-methyl-2-butanone—formic acid mixture gives a relative volatility of 5.2; 3/5 parts of DMSO with 3/5 parts of benzoic acid give 4.3. One third parts each of DMSO, benzoic acid and isophorone with one part of the 3-methyl-2-butanone—formic acid mixture gives a relative volatility of 3.5; with 2/5 parts, these three give 5.3. In every example in Table 1, the starting material is the 3-methyl-2-butanone—formic acid azeotrope which possesses a relative volatility of 1.0.

Two of the agents, DMSO and heptanoic acid, listed in Table 1 and whose relative volatility had been determined in the vapor-liquid equilibrium still, were then evaluated in a glass perforated plate rectification column possessing 5.3 theoretical plates and the results listed in Table 2. The data in Table 2 was obtained in the following manner. The charge was 75 grams of 3-methyl-2-butanone and 125 grams of formic acid and after a half hour of operation in the 5.3 theoretical plate column to establish equilibrium, DMSO and heptanoic acid at 92° C. and 64 ml/min. were pumped in. The rectification was continued with sampling of the overhead and bottoms after 30 minutes. The analyses are shown in Table 2 and were: overhead, 57.4% 3-methyl-2-butanone, 42.6% formic acid and bottoms was 23.3% 3-methyl-2-butanone, 76.7% formic acid which gives a relative volatility of 3-methyl-2-butanone to formic acid of 1.33. After 1¼ hours of continuous operation, overhead and bottoms were again sampled and analysed. The overhead was 55% 3-methyl-2-butanone, 45% formic acid and the bottoms was 15.4% 3-methyl-2-butanone, 84.6% formic acid which is a relative volatility of 1.44. This indicates that the relative volatility has been enhanced from 1.0 and separation accomplished by extractive distillation.

THE USEFULNESS OF THE INVENTION

The usefulness or utility of this invention can be demonstrated by referring to the data presented in Tables 1 and 2. All of the successful extractive distillation agents show that 3-methyl-2-butanone and formic acid can be separated from each other by means of distillation in a rectification column and that ease of separation as measured by relative volatility is considerable. Without these extractive distillation agents, the relative volatility would be 1.0 and separation by rectification would be impossible. The data also show that the most attractive agents will operate at a boilup rate low enough to make this a useful and efficient method of recovering high purity 3-methyl-2-butanone and formic acid from any mixture of these two including the azeotrope. The stability of the compounds used and the boiling point difference is such that complete recovery and recycle is obtainable by a simple distillation and the amount required for make-up is small.

WORKING EXAMPLES

Example 1

Twenty-five grams of 3-methyl-2-butanone, 75 grams of formic acid, 25 grams of DMSO and 25 grams of decanoic acid were charged to a vapor-liquid equilibrium still and refluxed for 15 hours. Analysis indicated a vapor composition of 17.9% 3-methyl-2-butanone, 82.1% formic acid and a liquid copmposition of 4.8% 3-methyl-2-butanone, 95.2% formic acid which is a relative volatility of 4.3. Five grams of DMSO and five grams of decanoic acid were added and refluxing continued for another eight hours. Analysis indicated a vapor composition of 22.5% 3-methyl-2-butanone, 77.5% formic acid and a liquid composition of 6.7% 3-methyl-2-butanone, 93.3% formic acid which is a relative volatility of 4.1.

Example 2

Ninety grams of the 3-methyl-2-butanone—formic acid mixture, 17 grams of DMSO, 17 grams of octanoic acid and 17 grams of butyl benzoate were charged to the vapor-liquid equilibrium still and refluxed for 13 hours. Analysis indicated a vapor composition of 27.7% 3-methyl-2-butanone, 72.3% formic acid and a liquid composition of 8.8% 3-methyl-2-butanone, 91.2% formic acid which is a relative volatility of 4.0. Three grams each of DMSO, octanoic acid and butyl benzoate were added and refluxing continued for another 14 hours. Analysis indicated a vapor composition of 27.1% 3-methyl-2-butanone, 72.9% formic acid and a liquid composition of 7.4% 3-methyl-2-butanone, 92.6% formic acid which is a relative volatility of 4.6.

Example 3

A glass perforated plate rectification column was calibrated with methyl cyclohexane and toluene which posseses a relative volatility of 1.46 and found to have 5.3 theoretical plates. A solution comprising 75 grams of 3-methyl-2-butanone and 125 grams of formic acid was placed in the stillpot and heated. When refluxing began, an extractive agent comprising 50% DMSO and 50% heptanoic acid was pumped into the column at a rate of 15 ml/min. The temperature of the extractive agent as it entered the column was 92° C. After establishing the feed rate of the extractive agent, the heat input to the 3-methyl-2-butanone and formic acid in the stillpot was adjusted to give a total reflux rate of 64 ml/min. After 30 minutes of operation, the overhead and bottoms samples of approximately two ml. were collected and analysed by gas chromaography. The overhead analysis was 57.4% 3-methyl-2-butanone and 42.6% formic acid. The bottoms analysis was 23.3% 3-methyl-2-butanone and 76.7% formic acid. Using these compositions in the Fenske equation, with the number of theoretical plates in the column being 5.3, gave an average relative volatility of 1.33 for each theoretical plate. After 1¼ hours of continuous operation, the overhead analysis was 55% 3-methyl-2-butanone, 45% formic acid, the bottoms analysis was 15.4% 3-methyl-2-butanone and 84.6% formic acid which is a relative volatility of 1.44. These data are presented in Table 2.

We claim:

1. A method for recovering 3-methyl-2-butanone from a mixture of 3-methyl-2-butanone and formic acid which comprises distilling a mixture of 3-methyl-2-butanone and formic acid in a rectification column in the presence of about one part of an extractive agent per part of 3-methyl-2-butanone—formic acid mixture, recovering 3-methyl-2-butanone as overhead product and obtaining the formic acid and the extractive agent from the stillpot, wherein said extractive agent consists of dimethyl sulfoxide and at least one material selected from the group consisting of hexahydrophthalic acid, myristic acid, p-nitrophenyl acetic acid, phenyl acetic acid, 2-methoxyethyl ether, diisobutyl ketone, ethyl phenyl acetate and diethyl maleate.

* * * * *